United States Patent [19]
Müller et al.

[11] Patent Number: 5,814,095
[45] Date of Patent: Sep. 29, 1998

[54] IMPLANTABLE MICROPHONE AND IMPLANTABLE HEARING AIDS UTILIZING SAME

[75] Inventors: Gerd Müller, Unterschleissheim; Hans Leysieffer, Taufkirchen, both of Germany

[73] Assignee: Implex GmbH Spezialhorgerate, Ismaning, Germany

[21] Appl. No.: 816,633

[22] Filed: Mar. 13, 1997

[30] Foreign Application Priority Data

Sep. 18, 1996 [DE] Germany ............ 196 38 158.4
Sep. 18, 1996 [DE] Germany ............ 196 38 159.2

[51] Int. Cl.$^6$ .......... H04R 25/00; A61F 11/04; A61B 1/375
[52] U.S. Cl. .......................... 607/57; 607/56
[58] Field of Search ............. 607/55–57

[56] References Cited

U.S. PATENT DOCUMENTS

| | | |
|---|---|---|
| 3,346,704 | 10/1967 | Mahoney . |
| 3,557,775 | 1/1971 | Mahoney . |
| 3,712,962 | 1/1973 | Epley . |
| 3,764,748 | 10/1973 | Branch et al. . |
| 3,882,285 | 5/1975 | Nunley et al. . |
| 4,134,408 | 1/1979 | Bownlee et al. . |
| 4,352,960 | 10/1982 | Dormer et al. . |
| 4,532,930 | 8/1985 | Crosby et al. . |

(List continued on next page.)

FOREIGN PATENT DOCUMENTS

| | | |
|---|---|---|
| 619689 | 1/1992 | Australia . |
| 624989 | 6/1992 | Australia . |
| 0 179 536 | 4/1986 | European Pat. Off. . |
| 0 076 070 | 8/1986 | European Pat. Off. . |
| 0 263 254 | 4/1988 | European Pat. Off. . |
| 0 499 939 | 8/1994 | European Pat. Off. . |
| 0 499 940 | 8/1994 | European Pat. Off. . |

(List continued on next page.)

OTHER PUBLICATIONS

*Implantable Hearing Aid—Report Of The First Human Applications,* Naoaki Yanagihara et al., Arch Otolaryngol Head Neck Surg., vol. 113, Aug., 1987.

Hiroshi Wada et al;, "Analysis of dynamic behavior of human middle ear using a finite–element method", Dec. 1992, pp. 3157–3168.

(List continued on next page.)

*Primary Examiner*—William E. Kamm
*Assistant Examiner*—Carl H. Layno
*Attorney, Agent, or Firm*—Sixbey, Friedman, Leedom & Ferguson; David S. Safran

[57] ABSTRACT

Implantable microphone for implantable hearing aids, which is used for excitation of hearing, such as cochlear implants or hearing aids with mechanical stimulation of the middle or inner ear, with a microphone capsule which is accommodated in a hermetically sealed housing, and with an electrical lead-in wire connector for connecting an implant line to the microphone module. The housing has at least two legs which are oriented at an angle relative to one another, one leg holding the microphone capsule and being provided with a sound inlet membrane, and the other leg containing the electrical lead-in wire connector. As a result of the two-legged geometry of the microphone housing, the microphone can be implanted after a mastoidectomy in the mastoid cavity such that the leg which has the sound inlet membrane lies in a hole in the posterior wall of the auditory canal so that, by mechanical contact of the membrane with the closed skin of the auditory canal wall, an acoustic signal incident in the external auditory canal is acoustically received, while the leg of the microphone housing containing the electrical lead-in wire connector is in the area of the mastoid tip. Completely implantable hearing aids for electrical excitation of hearing using the implantable microphone, can have, on the implant side, a battery arrangement for power supply which can be recharged transcutaneously via an external charging device. The audiological implant functions can, likewise, be transcutaneously controlled via a remote control.

30 Claims, 4 Drawing Sheets

U.S. PATENT DOCUMENTS

| | | |
|---|---|---|
| 4,729,366 | 3/1988 | Schaefer . |
| 4,850,962 | 7/1989 | Schaefer . |
| 4,988,333 | 1/1991 | Engebretson et al. .................... 607/57 |
| 5,015,224 | 5/1991 | Maniglia . |
| 5,015,225 | 5/1991 | Hough et al. . |
| 5,176,620 | 1/1993 | Gilman . |
| 5,279,292 | 1/1994 | Baumann et al. . |
| 5,411,467 | 5/1995 | Hortmann et al. . |

FOREIGN PATENT DOCUMENTS

| | | |
|---|---|---|
| 0 572 382 | 7/1995 | European Pat. Off. . |
| 0 400 630 | 8/1995 | European Pat. Off. . |
| 1 940 803 | 3/1970 | Germany . |
| 34 20 244 | 12/1985 | Germany . |
| 39 18 086 | 9/1990 | Germany . |
| 39 18 329 | 12/1990 | Germany . |
| 39 40 632 | 12/1990 | Germany . |
| 41 04 359 | 11/1992 | Germany . |
| WO89/06988 | 8/1989 | WIPO . |
| WO/9208330 | 5/1992 | WIPO . |
| WO92/09181 | 5/1992 | WIPO . |
| WO92/22107 | 12/1992 | WIPO . |
| WO93/06666 | 4/1993 | WIPO . |

OTHER PUBLICATIONS

A. E. Deddens et al, "Totally implantable hearing Aids: The effects of skin thickness on microphone function", 1990, pp. 1–4.

M. Hoke et al, "Advances in Audiology and Middle Ear Implant: implantable hearing aids", 1998, pp. 67–123.

IMPLANTABLE MICROPHONE AND IMPLANTABLE HEARING AIDS UTILIZING SAME

BACKGROUND OF THE INVENTION

1. Field of the Invention

The present invention relates to the field of partially or fully implantable electronic systems for the rehabilitation of sensory hearing disturbances by stimulation of the auditory nerve with electrical stimulation signals, and in particular, to an implantable microphone and implantable hearing aids using an implantable microphone.

2. Description of Related Art

Electrical hearing prostheses which stimulate hearing by direct electrical stimulation via active electrodes have now reached a level of development which allows routine implantation in those patients whose hearing has completely or almost completely failed due to accident, disease or other influences, or which has not functioned since birth. If, in these cases, only the inner ear (cochlea) and not the centrally guiding neuronal auditory path is affected, using electrical stimulation signals, the remaining auditory nerve can be stimulated, and thus, an auditory impression can be produced which can lead to clear speech understanding with appropriate electronic audio signal processing. These systems are called cochlear implants according to conventional usage.

In these so-called cochlear implants, a single- or multi-channel active electrode array is inserted into the cochlea and is triggered by an electronic module, this electronic module being encapsulated in a hermetically sealed manner and is biocompatibly embedded by surgery in the bony area behind the ear (mastoid). However, the electronic module contains, essentially, only decoder and driver circuits for the active electrodes; acoustic sound reception, conversion of this audio signal into electrical signals and their further processing, essentially take place externally in a so-called speech processor which is worn externally on the body. The speech processor converts the preprocessed signals, generally digitally encoded in an appropriate manner, into a high frequency carrier signal which is transmitted via inductive coupling through the closed skin (transcutaneously) to the implant. The microphone which picks up the sound is located exclusively outside of the body, in most applications, in a housing of a behind-the-ear hearing aid (BtE) worn on the external ear, and it is connected to the speech processor by a cable. The speech processor obtains its operating energy from built-in primary batteries or rechargeable batteries. The implant, itself, does not contain any energy storage means which are electrically active over the long term, but acquires its operating energy from the high frequency, transcutaneously and inductively coupled carrier signal of the speech processor.

For the aforementioned reasons, all currently known and available cochlear implants are only partially implantable, i.e., the entire system is ready for operation only by the interplay of external and implantable components.

The scientific principles and clinical applications of cochlear implants are described in numerous publications; an outline of the current state of science and technology is given for example in: Merzenich, M. M. et al.: "Electrical Stimulation of the Acoustic Nerve in Man", Velo-Bind, San Francisco, 1974; Schindler, R. A. and Merzenich, M. M. (eds): "Cochlear Implants,", Raven Press, New York, 1985; Hoke, M. (ed): "Cochlear Implants in Clinical Use", Advances in Audiology, Vol. 2, Karger Basel, 1984; Miller, J. M. and Spelman, F. A. (eds): "Cochlear Implants", Springer N.Y., 1989; Hochmair-Desoyer, I. J. and Hochmair, E. S. (eds): "Advances in Cochlear Implants", MANZ Vienna, 1993, The technical versions of implant components and extracorporal parts of cochlear implants such as microphones, their electrical feed, speech processor embodiments, voice encoding strategies and principles of transcutaneous power and data transmission to the implanted system part are documented in numerous patent publications: European Patent Application 0 572 383 (Daly), International Patent Application WO-A-92/22107 (Kuzma), Australian Patent 624989 (Seligman and Dowell), U.S. Pat. No. 4,532,930 (Crosby et al), EP-A-0 076 070 (Hochmair), Australian Patents 314490 (Dooley et al.) and 6776784 (Harrison and Seligman), International Patent Application WO-A-89/06988 (Kuzma), German Patent Application 34 20 244 (Hortmann and Kunick), and Australian Patent 619689 (Seligman).

The basic disadvantage of all the aforementioned cochlear implant systems, which apply especially in the currently recognizably effective and reliable supply in children, consists in that a speech processor, an external microphone, a transmitting coil and associated cable connections which are fundamentally necessary to operate the implant, must be worn externally on the child's body. This poses a disability in everyday life and stigmatization of the patient by the visible external components of the hearing prosthesis.

These major disadvantages can only be completely circumvented by implanting the cochlear implant in its entirely with all technically necessary operating components. This requires the following clinical and technical solutions:

A) The electronic signal processing system must be integrated into the implant;

B) The power supply of the entire system must be made to be implantable; and

C) The sound-receiving microphone must be designed such that it can, likewise, be implanted completely under the closed surface of the body.

With respect to A):

Modern microelectronics currently makes available forms of miniaturization which enable complete integration of all necessary signal processing components with minimized electrical power consumption. This applies especially to completely implanted devices because, in this case, the transcutaneous high frequency transmission path for data and operating power which is complex in terms of technology and energy is unnecessary.

Relative to B):

One possibility for powered operation of an active implant is to integrate a primary battery, This is known from the prior art of cardiac pacemakers. With a higher demand for continuous operating power as in the case of an active hearing aid, an electric battery can be integrated into the implant which, only if necessary, after discharging, is recharged transcutaneously from the outside by inductive means. These power supply systems have been described, for example, for cardiac pacemakers (German Patent Application 19 40 803 and U.S. Pat. No. 4,134,408). In the case of implantable hearing prostheses, these rechargeable battery systems have been indicated especially for hearing aids with electromechanical stimulation of a damaged inner ear (German Patent Application 41 04 359, U.S. Pat. No. 5,279,292, European Patent Application 0 499 939, German Patent Application 39 18 086, European Patent Application 0 400 630, and U.S. Pat. No. 5,411,467).

In connection with C):

Fundamental design possibilities of an implantable microphone for hearing aids have, likewise, been described for hearing aids with electromechanical stimulation. Schaefer (U.S. Pat. Nos. 4,729,366 and 4,850,962 and European Patent Application 0 263 254) describes an implantable hearing aid in which, after removal of the iucus of the ossicular chain, a double converter system is used, one element being used as the mechanical-electrical converter (sensor:microphone function) and the other element as an electromechanical converter for vibrational stimulation of the stapes (actuator function). The sensor element is joined to the remaining malleus via a coupling element which is made of mechanically stiff wire, and thus, picks up the mechanical vibrations of the eardrum which result from an acoustic wave incident on it. For sensor coupling, different versions of the coupling element to the handle of the malleus, the head of the malleus, and the body of the malleus are described. The following aspects appear to be problematic in the described microphone implementation:

When using a piezoceramic converter element which is made, for example, as a rod-shaped bimorph flexural vibrator, the mechanical input impedance is clearly above the biological mechanical source impedance which, in this case, is formed mainly by the eardrum system with the malleus which is fused with it. At the given input acoustic pressure level in the external auditory canal, this results in a very small deflection of the piezoelement; this, in turn, leads to very small electrical output signals at a given mechanical-electrical conversion factor of the piezoelement. The high electrical amplification in the signal-processing module which is therefore necessary reduces the useful dynamics of the overall system due to an insufficient signal-to-noise ratio in current microelectronic amplifier technology.

Even if the aforementioned disadvantage is diminished by using a converter system with a clearly reduced mechanical impedance level, for example, thin piezofilms (for example, polyvinylidene fluoride, PFDV), another disadvantage of this version of a microphone function remains. In particular, based on the currently known complex resonance properties of the middle ear apparatus including the eardrum (for example, "Analysis of dynamic behavior of human middle ear using a finite-element method", Wada. H. et al. J. Acoust. Soc. Am. 92 (6), December 1992, pp. 3157–3168), it cannot be assumed that, at the accepted initial acoustic pressure, which is independent of frequency, an acoustic pressure response which is likewise flat with respect to frequency is achieved. This results in linear distortions of the microphone transmission function which are undesirable for the desired hearing aid function, and in addition, are subject to fluctuations among individuals due to anatomy differences.

The technical implementation of the necessary hermetically sealed and biocompatible encapsulation of the sensor element, which is not detailed, seems especially very difficult as well since the mechanical vibrations of the coupling wire which joins the hammer to the converter element must be routed through the necessarily hermetically sealed wall of the implant housing which contains the active converter element.

Engebretson et al. (U.S. Pat. No. 4,988,333) describe an implantable acoustic coupler system in which a chamber closed with a thin circular membrane consisting, for example, of silicone is made as the sound-receiving element. This membrane can be joined, for example, mechanically securely to the malleus of the ossicular chain via a thin coupling wire which is attached in the center of the membrane, by which the eardrum vibrations are replicated as an audio signal within the chamber. Via a sound conduction tube which is connected to this receiving coupling chamber, the audio signal is routed to a microphone which is not housed in the mastoid cavity for reasons of space, but is, instead, in a main implant housing in the area of the antrum or the mastoid. This system was tested in a miniaturized embodiment (4.0 mm diameter of the coupling chamber) in its fundamental operation in a two-week animal model (Deddens et al.: "Totally implantable hearing aids: the effects of skin thickness on microphone function", Am. J. Otolaryngol. 1990, 11, pp. 1–4), in which the acoustic coupling chamber was closed with a 100 micron thick silicone disk as the sound inlet membrane.

The basic principle of acoustic conduction via a tube element is described by other authors (Mahoney, U.S. Pat. Nos. 3,346,704 and 3,557,775, and Nunley et al., U.S. Pat. No. 3,882,285, and Leysieffer et al., German Patent Application 39 40 632). The actual microphone element is placed, in all described cases, in an encapsulated implant housing. Sound is delivered into this microphone via a mechanically rigid or flexible tube which has an input end which is closed, for example, with a thin membrane via which the incident acoustic is received. The sound reception site in Mahoney is the area of the mastoid behind the outer ear (tube end with membrane under the closed skin over the mastoid), the area of the outer auditory canal in which the supply tube is covered by the thin skin of the wall of the auditory canal, in Nunley et al., and the mastoid cavity, itself, into which projects the end of the sound supply tube which is closed with a thin membrane in Leysieffer et al.

In these solutions, the following aspects seem problematic or technically difficult to implement:

In addition to the actual microphone, additional bulky elements are necessary which make implantability difficult under the space conditions in the area of the middle ear, antrum and mastoid, which are very limited anyway, and which make the biostability which is required under long term aspects appear questionable.

Technically, under the aspects of water vapor absorption of silicones in percent by volume which are generally known today, the membrane which closes the tube elements or coupling chambers on the acoustic input side, the hermetic tightness of the implant required for long-term stability cannot be accomplished, i.e., there is the major risk that, on the one hand, the electronic implant components, such as especially the microphone itself, can be destroyed or damaged by moisture which enters, and on the other hand, toxic substances can emerge from the implant and can penetrate into the body tissues. Functionally, there are similar limitations on the individually reproducible amount of transmission of these microphone systems which is independent of frequency, as in the Schaefer system (see above), since the thin membranes and sound-conducting tubes can cause linear distortions which, in the individual case, must be balanced with expensive electronic measures.

Another version is given by Suzuki and Yanigahara ("Middle Ear Implants: Implantable Hearing Aids", Hoke, M. (ed), Advances in Audiology, Vol. 4, Karger Basel, 1988). A cylindrical, high-quality steel housing is hermetically sealed on one side with a circular, thin, high-quality steel membrane. Within this housing is a conventional miniature electret microphone with a sound inlet opening which projects into a likewise sealed intermediate space which is formed by the housing membrane and an internal intermediate wall. The three electric microphone connections are routed out of the high-quality steel housing via a three-pin sealed signal feed through, which is placed next to the microphone capsule, and they are joined to the adjoining implantable microphone connecting line. The housing interior is filled with an inert gas (argon) for reasons of corrosion protection. The housing is implanted in the mastoid cavity such that the housing side with the circular membrane is placed in a corresponding hole in the posterior wall of the auditory canal, and the skin of the auditory canal is in direct mechanical complete contact with the thin high-quality steel membrane. When an acoustic wave is incident in the auditory canal, the metal membrane with the overlying skin of the auditory canal is caused to mechanically vibrate; this leads to a pressure fluctuation in the small-volume intermediate space in the interior of the housing. This pressure fluctuation is picked up by an internal microphone as a corresponding acoustic signal and is converted into an electrical signal which can be delivered via a connecting line to the electronics for further processing. Here, the system is designed such that the first mechanical resonance of the vibratory metal membrane is spectrally on the upper end of the audiologic transmission range and the amount of transmission of acoustic pressure below this resonance is independent of frequency, and thus, no linear distortions occur. The skin of the auditory canal essentially represents an additive dynamic mass coating for the vibratory membrane, so that the resonant frequency for coating with skin compared to no-load without the skin coating is shifted simply to lower frequencies, without the amount of transmission, and thus the total microphone frequency sensitivity, changing. The design is such that the resonant frequency in the implanted state, i.e., with the skin coating of the auditory canal, is 3 to 5 kHz, and thus, at least fundamentally, the audiologically important frequency range can be transmitted. Roughly 2 mV/Pa is given as the acoustic pressure response. This value is called adequate for further electronic processing with acceptable signal-to-noise ratio. The external dimensions of this cylindrical microphone module are 8.0 mm in diameter and 4.0 mm in height.

This system has the following advantages compared to the other embodiments of an implantable microphone cited here:

Based on the all-metal implementation, the module is hermetically sealed and thus protected against bodily fluids.

The functional form of the sound-receiving membrane enables an acoustic pressure response which is largely independent of the frequency up to the first resonant frequency.

Mismatching of the mechanical system of the membrane relative to the acoustic impedance of the incident acoustic wave remains within an acceptable range, so that a technically useful response results.

However, due to its external geometry this module has a major disadvantage. That is, our own extensive clinical determinations have shown that it is impossible to place a cylindrical module with a total diameter of 8.0 mm in the bony area of the auditory canal, and thus, in a hole in the auditory canal wall such that, on the one hand, complete coverage of the circular flat surface with the auditory canal skin takes place, and on the other hand, it can be ensured that this module can be biostably implanted for the long term. This is essentially due to the fact that, first of all, the external auditory canal has a diameter that is less than 10 mm, and thus, a circular membrane with a 8.0 mm diameter cannot be a contacting tangential surface, but rather represents a cutting plane, and secondly, removal of such a large bony area in the auditory canal wall makes the availability an adequate amount of the auditory canal skin remaining above the metal membrane extremely questionable. Overall, it seems very doubtful whether the described microphone system can be implanted at all in the bony area of the auditory canal or whether placement is possible only in the cartilaginous or soft part area of the auditory canal. In the latter case, there is recognizably the high risk of migration of the implant, since adequate; mechanically strong and long term-stable anchoring of the microphone housing in the bony structures is not possible.

It is clear from the prior art that synthesis of a completely implantable cochlear implant or hearing aid is based essentially on a technically and clinically feasible implementation of a proper microphone which is not currently available for the reasons described.

SUMMARY OF THE INVENTION

Therefore, a primary object of this invention is to devise an implantable microphone for implantable hearing aids which can be reliably implanted with long term stability.

Another primary object of this invention is to devise a completely implantable hearing aid for electrical stimulation of hearing.

It is a related object to provide such a hearing aid which can be implanted with long-term stability and with which the above described problems of known hearing aids are overcome.

To achieve these objects, this invention provides a completely implantable microphone for use in implantable hearing aid systems which is based on the principle of the hermetically sealed membrane housing described by Suzuki and Yanigahara, but which enables, by means of a fundamentally modified housing geometry, a clear reduction of the outside dimensions while maintaining or improving the functional operating parameters, this geometry being matched to the given natural anatomical conditions of the implantation site in the area of the mastoid cavity and the rear auditory passage wall.

In particular, in an implantable microphone for an implantable hearing aid which is used for excitation of hearing having a microphone capsule which is hermetically sealed on all sides in a housing and with an electrical lead-in wire connector for routing at least one electrical connection from the interior of the housing to its outside, according to the invention, the housing has at least two legs which are oriented at an angle relative to one another, one leg holding the microphone capsule and being provided with a sound entry membrane, and the other leg containing the electrical lead-in wire connector and being set back relative to the plane of the sound entry membrane.

With regard to audiological aspects, the optimum sound reception site for an implantable membrane is considered the low-lying area of the auditory canal, since there, near the biologically natural site of the eardrum, the acoustic properties of the outer ear and the auditory canal can be used for directionally-dependent filtering out of the noise signals. The configuration of the microphone housing explained here makes it possible to minimize the geometrical dimensions of the housing part provided with the sound inlet membrane to such an extent that the sound-receiving membrane can have a diameter of less than 5.0 mm. Our own detailed clinical studies have shown that almost flat matching to the roughly circular cross section of the auditory canal in the lower-lying bony area is possible with this membrane diameter. This minimized diameter is determined by the dimensions of the smallest currently available miniature electret microphone. Internal placement of the additionally necessary electronic components and of the electrical feed throughs for connection of the module next to the microphone capsule, as in the embodiment of Suzuki and Yanigahara, is not possible here. The microphone housing must be routed, after a mastoidectomy, out of the mastoid into a hole made in the rear auditory canal wall and placed there such that mechanically reliable contact of the entire membrane surface is achieved with the auditory canal skin which lies above the hole.

The preferably cylindrical area of the microphone housing provided with the sound inlet membrane, therefore, preferably has at least a length which corresponds to the statistical maximum of the thickness of the posterior wall of the auditory canal. The distance of the sigmoid sinus, which has external contours which may not be changed surgically for clinical reasons, to the rear auditory canal wall has been found to essentially determine the geometry and volume for the microphone housing to be redesigned. This distance, which is very small under many individual anatomic conditions, structurally does not allow an overall axial arrangement of the internal microphone capsule, electronic components and the necessary sealed signal feed through for electrical connection of the microphone.

Therefore, according to the invention, the basic geometry of the microphone housing is selected such that this housing is formed essentially of two legs which are arranged at an angle to one another, one leg which is preferably made cylindrical, containing the microphone capsule and the sound-receiving, preferably circular membrane, and the other leg holding the electrical lead-in wire connector and preferably electronic components as are detailed below.

In particular, for the aforementioned reasons, the geometry of the microphone housing is preferably selected such that, when the microphone is implanted in the mastoid cavity, the leg which contains the sound inlet membrane projects out of the mastoid into an artificial hole in the posterior wall of the auditory canal and the sound inlet membrane touches the skin of the auditory canal wall, and that the leg of the microphone housing which contains the electrical lead-in wire connector is placed in the area of the mastoid tip. Expansion of the mastoid cavity above and beyond a complete mastoidectomy is not necessary for this purpose.

Since the surgical placement of the described microphone module takes place such that the end of the housing leg which contains the lead-in wire connector points in the direction of the mastoid tip, it is practical for an electrical line connected to the lead-in wire connector in the connection area to be at a right angle to the housing leg containing the electrical lead-in wire connector. In this way, a sharp kink or a very small bending radius of the line is prevented which otherwise would be caused by the anatomy of the opened mastoid cavity in the area of the mastoid tip, and the line connection to the microphone module is thus unloaded with respect to continuous mechanical stresses.

The electrical lead-in wire connector can be of a multi-pin design. For a two-pin version, the arrangement is such that it operates using the electrical principle of phantom feed, i.e., one pin carries the useful signal potential and the power-supply DC voltage potential jointly for microphone power supply. If the electrical lead-in wire connector is made single-pin, this one pin can carry the useful signal potential and the power-supply DC voltage potential together, while a second pin of a feeding line is connected to the microphone housing, which is made electrically conductive for this purpose, and which carries the ground potential by internal connection with the microphone capsule wiring.

Regardless of the version of internal acoustic conversion into an electrical signal, the electronic components needed for electrical connection of the internal microphone capsule according to the principle of phantom feed are accommodated preferably likewise in the microphone housing, especially in the housing leg which holds the electrical lead-in wire connector. Furthermore, the microphone housing can contain electronic components which enable electrical impedance conversion and/or electrical signal amplification and/or protective measures against ambient electrical, magnetic and/or electromagnetic influences. These latter measures generally include high frequency capacitors and varistors in order, on the one hand, to protect the microphone module itself against destruction due to high-energy electromagnetic action, and on the other hand, to minimize or suppress capacitive and inductive interference in the signal path which can lead to problems in audio signal processing of the implant system connected to the microphone module.

The microphone housing, including the sound-receiving membrane and the electrical feed throughs is made preferably with biocompatible metals, for example, pure titanium or biocompatible titanium alloys, and is hermetically sealed in a gas tight manner on all sides.

The microphone capsule located in the microphone housing is designed especially for operation according to the electrodynamic, electromagnetic, dielectric, and preferably, according to the electret principle. In particular, it can also be an electret miniature version with integrated field effect transistor for electrical impedance conversion. The microphone can also be made according to the capacitor microphone principle in an audio frequency or high frequency circuit. Still further, the microphone function can be accomplished by a semiconductor microphone in silicon technology which is made using procedures of microsystem engineering.

In order to make the electrical connecting line which joins the microphone module to the hearing aid implant system largely invulnerable to ambient electromagnetic influences (EMV), this connecting line is preferably formed as a twisted pair or coaxial line.

The implantable microphone described here can be a component of partially or fully implantable hearing aids such as, for example, cochlear implants for electrical stimulation of the auditory path, hearing aids for mechanical stimulation of the middle ear or the inner ear, and active masking systems for tinnitus treatment which, with proper electronic signal processing and power supply systems and stimulation means, enable rehabilitation of partial or complete failure or apparatus treatment of impairment of one or both hearing organs.

The generic term hearing aids generally includes partially or fully implantable systems which enable, using the described microphone module, proper electronic signal processing and power supply systems and stimulation means, the rehabilitation of partial or complete failure or apparatus treatment of impairment of one or both hearing organs. They also include especially cochlear implants with electrical stimulation of the auditory path, implantable hearing aids with mechanical stimulation of the middle ear or the inner ear, and active, implantable masking systems for tinnitus treatment.

These and further objects, features and advantages of the present invention will become apparent from the following description when taken in connection with the accompanying drawings which, for purposes of illustration only, show several embodiments in accordance with the present invention.

DETAILED DESCRIPTION OF THE PREFERRED EMBODIMENTS

Figure 1:
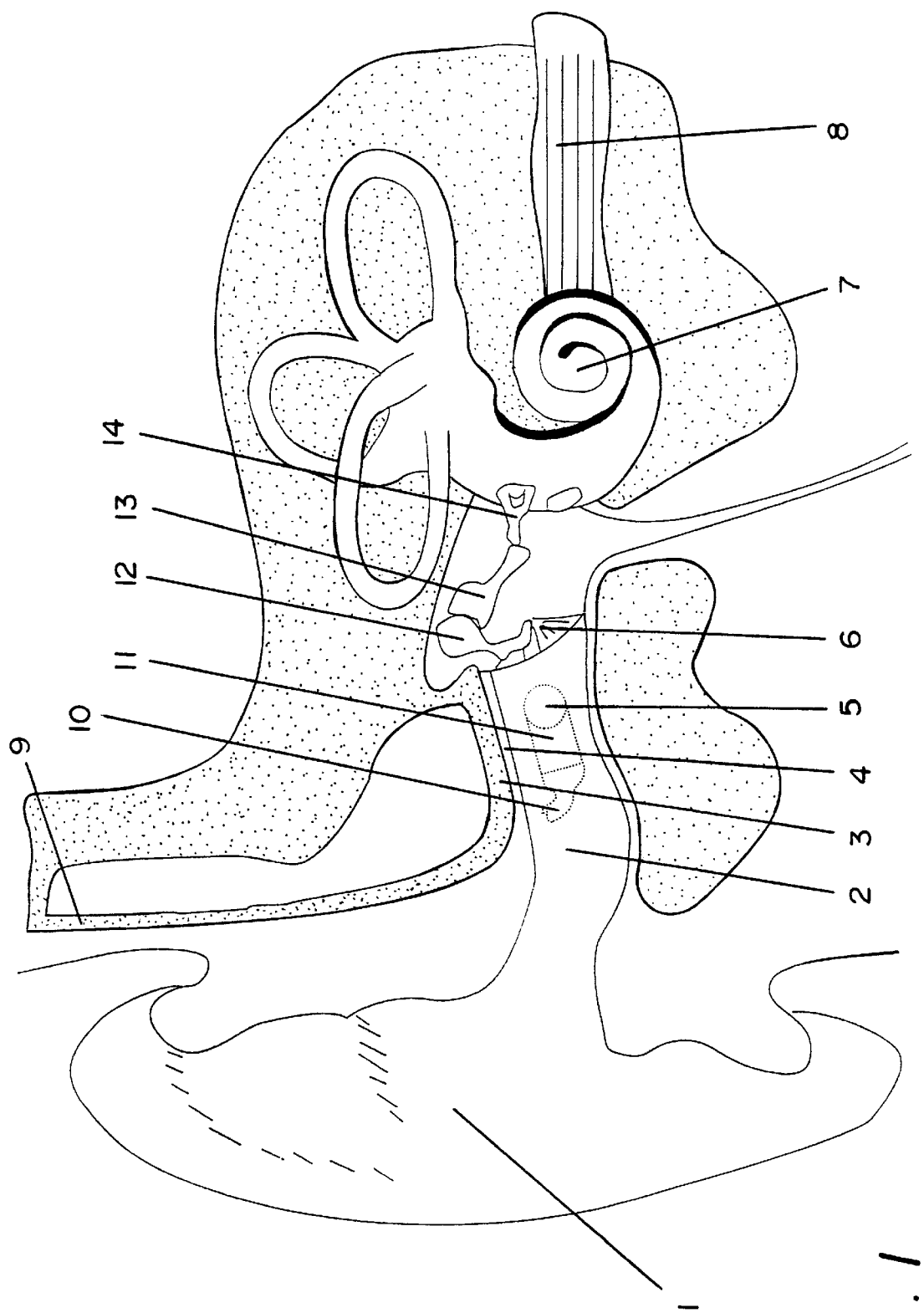
FIG. 1 shows a cross section through a human ear with an implanted microphone module.
Figure 2:
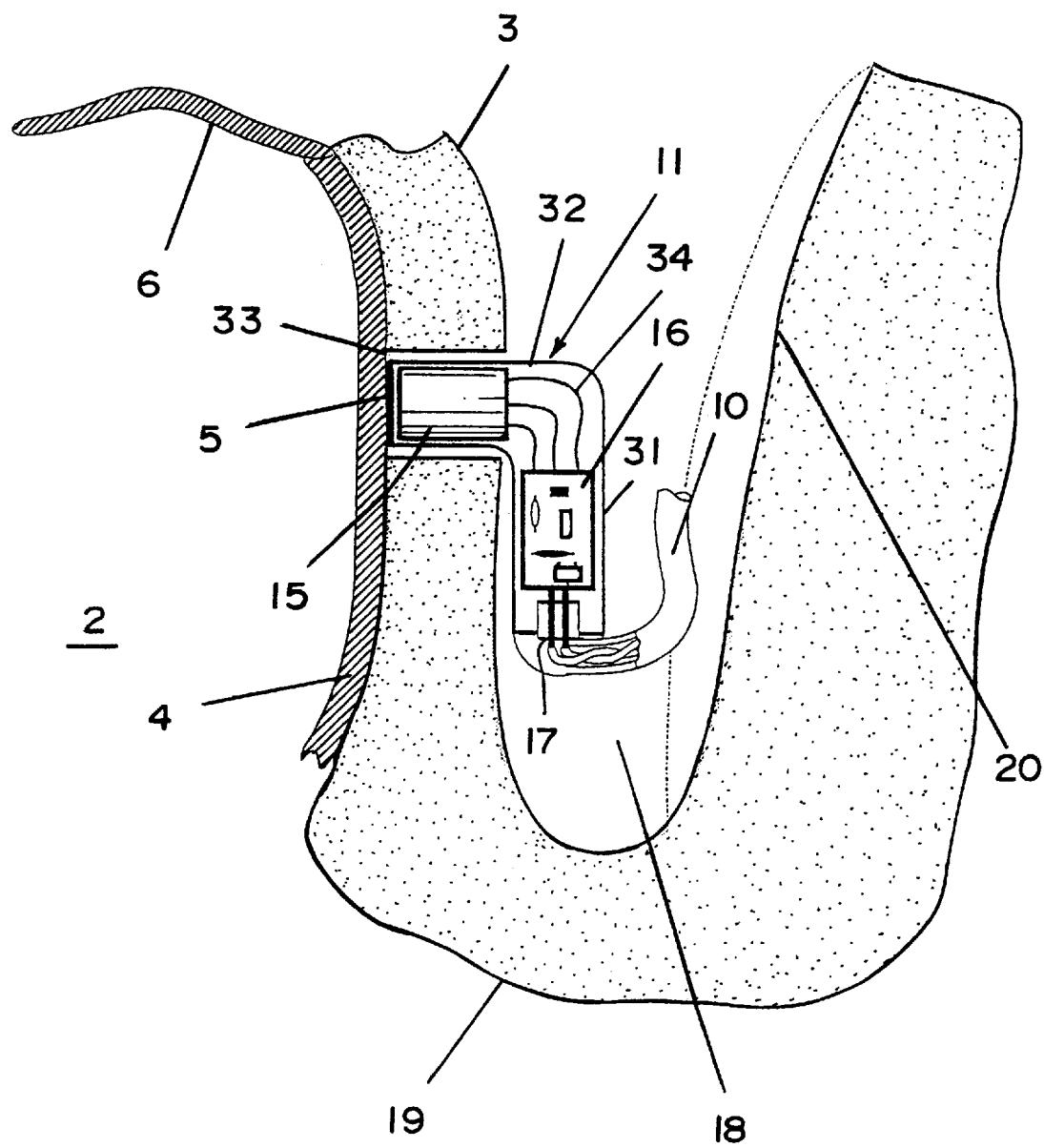
FIG. 2 is an overhead view into the mastoid cavity with a microphone module implanted therein after a completed mastoidectomy.

FIG. 1 shows a cross section through a human ear having an outer ear 1, auditory canal 2, posterior wall of the auditory canal 3, skin 4 of the auditory canal, eardrum 6, the ossicular chain consisting of malleus 12, iucus 13, and stapes 14, inner ear (cochlea) 7 and auditory nerve 8. A microphone module which has microphone housing 11, and which is placed in the area of the posterior wall of the auditory canal of mastoid 9 is shown in phantom outline drawn roughly to scale in the implanted state, the skin 4 of the auditory canal wall touching a membrane 5, which forms part of microphone housing 11. As can be seen in FIG. 2, a first leg 31 of microphone housing 11 contains an electrical lead-in wire connector 17 within connection line 10 which, in the implanted state, points roughly in the direction of the mastoid tip 19.

FIG. 2 shows microphone housing 11 in the implanted state in mastoid cavity 18 after a mastoidectomy. A second leg 32 of the microphone housing 11 which holds microphone capsule 15 is inserted into a corresponding artificial hole 33 in bony auditory canal wall 3, such that the skin 4 of the auditory canal touches circular membrane 5 in a mechanically reliable manner over the entire circular surface of the membrane 5. The area of the skin of the auditory canal wall which touches the membrane 5, together with the membrane, represents a mechanically oscillatory formation which is caused to vibrate mechanically by an acoustic wave incident with eardrum 6 in external auditory canal 2; these mechanical vibrations are replicated as acoustic pressure fluctuations in the hermetically sealed inner volume of microphone housing 11. These pressure fluctuations are converted by internal microphone capsule 15 into an electrical signal which is delivered to signal processing unit 16 via internal electrical lines 34.

Signal processing unit 16 can contain components for electrical phantom feed of the system, active amplifying elements, impedance-converting components, and components for suppression or attenuation of electrical, magnetic, and/or electromagnetic ambient influences. Signal processing unit 16 is electrically connected on the output side to lead-in wire connector 1 7 which is inserted into microphone housing 11 in a hermetically sealed manner. Signal processing unit 16, together with lead-in wire connector 17, is accommodated in the first leg 31 of microphone housing 11 which is at an angle, here shown preferably as a right angle, to second leg 32 of the microphone housing 11, which is provided with the sound-receiving membrane 5 and which contains internal microphone capsule 15. Electrical line 10 is preferably connected at a right angle to electrical lead-in wire connector 17 such that line 10 can be routed out of mastoid tip 19 without kinks and avoiding very small bending radii. Electrical lead-in wire connector 17 and line 10 are made with two pins and wires, here, for the preferable case of power supply of the microphone module via phantom feed in which the useful signal AC voltage and supply DC voltage are routed jointly via one pin and the ground signal via a second pin. In this case, the line arrangement of electrical implant line 10 is made preferably according to the twisted pair principle in order to minimize ambient electromagnetic effects on implant line 10.

FIG. 2 shows the restricted space conditions in the opened mastoid cavity which are dictated essentially by the distance between the posterior wall of the auditory canal 3 and the bony wall of sigmoid sinus 20 which contains an important venous supply and therefore cannot be surgically removed. Only accommodating the described components in a two-legged housing allows the choice of the described implantation site. An axial arrangement of all microphone module components, including the electrical line connection, is not possible. Furthermore, FIG. 2 shows that first leg 31 of microphone housing 11 which contains lead-in wire connector 17 must be set back by at least the thickness of bony auditory canal wall 3 relative to the plane of circular housing membrane 5 in order to ensure insertion of housing 11 deep enough into the artificial hole 33 in the auditory canal wall for the membrane 5 of the microphone housing to reliably touch the skin 4 of the auditory canal wall in all areas of the membrane.

FIGS. 1 and 2 show that microphone housing 11 should be placed with leg 31, which contains lead-in wire connector 17 and connected electrical line 10, preferably in the direction toward mastoid tip 19 if, in the case of a fully implantable electromechanical hearing aid, components of the electromechanical converter are implanted in the mastoid cavity, antrum or directly in the middle ear region.

There can be a different orientation of the microphone housing, i.e. one degree of freedom of the surgical placement of the microphone module if, in the case of a fully implantable hearing aid with direct electrical stimulation of the cochlea, only the corresponding active electrode array needs to be guided out of the mastoid in the direction of the cochlea, and thus, the above described highly limited space and volume conditions are not present. These combinations of embodiments with the described microphone module are shown schematically in FIGS. 3 and 4.

Figure 3:
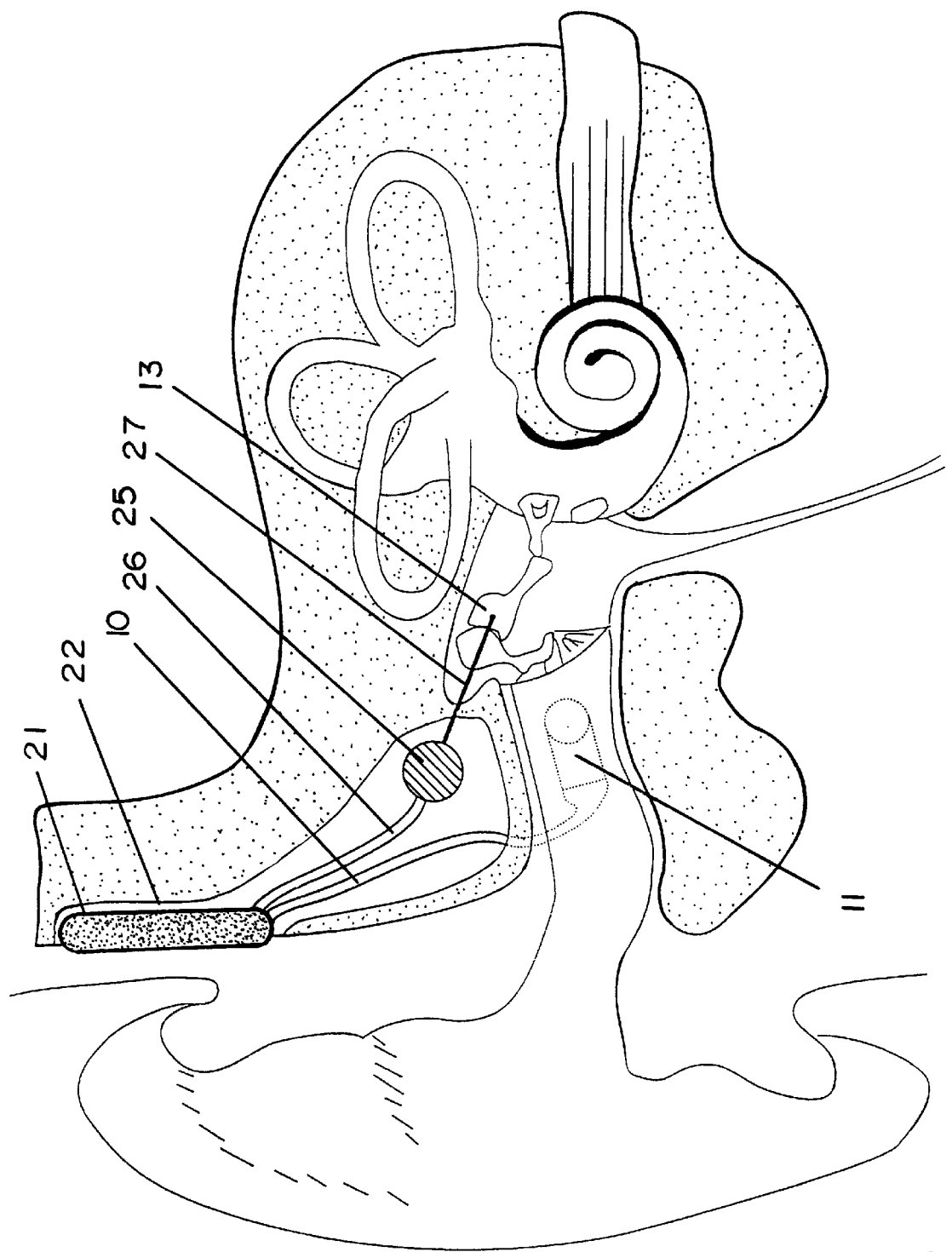
FIG. 3 shows application of the implantable microphone module in a completely implantable hearing aid for electromechanical stimulation of the ossicular chain.

FIG. 3 shows a fully implantable hearing aid with electromechanical stimulation of the ossicular chain using a microphone module accommodated in housing 11, signal processing unit 21, which can also contain, as noted above, an electric power supply and components for wireless communications with the outside world, and which is connected via line 10 to the microphone module, being accommodated in routed-out bone bed 22 in the mastoid area. Implant line 26, which carries the electrical output signal, leads to an electromechanical converter 25 which is placed, for example, in the mastoid cavity or the antrum. The mechanical vibrations of converter 25 are delivered via suitable mechanical coupling element 27 to the ossicular chain, for example, to the iucus 13, as shown.

Figure 4:
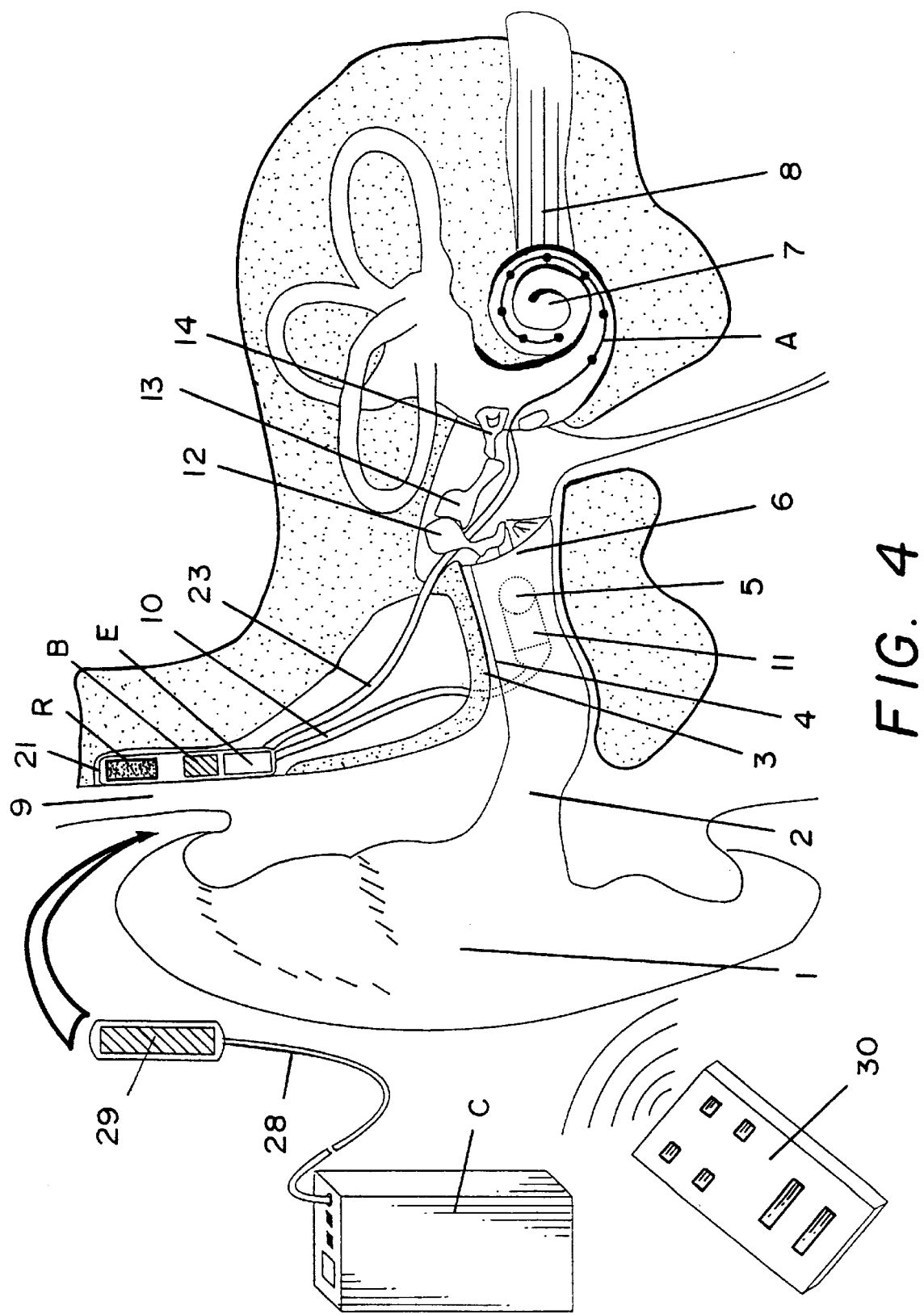
FIG. 4 shows application of the implantable microphone module to a completely implantable cochlear implant for direct electrical stimulation of the cochlea.

FIG. 4 shows another completely implanted hearing aid; but, in this case, direct electrical stimulation of hearing is produced by a receiving means in the form of an active electrode array A which is inserted into the cochlea 7, using the microphone module in housing 11. Here, the signal processing unit 21 is also placed with all components necessary for transcutaneous implant operation in a artificial bone bed 22 in the mastoid, and an electrical feed line 23 leads to an active electrode array 24, running from the mastoid through the area of the middle ear to the cochlea 7.

Electrical line 10 of the microphone leads to main electronic module/signal processing unit 21 which is housed in a routed-out area in the bony area of mastoid 9. Main electronic module/signal processing unit 21 contains a battery arrangement B comprised of one or more rechargeable batteries which can be nickel cadmium, nickel-metal-hydride, lithium, or lithium ion type power cells, receiving means R for receiving the transcutaneously and inductively supplied energy for recharging battery arrangement B, and an electronic unit E for audio signal processing and for control of the internal power supply which includes a telemetry means for data communications with the outside world. From main electronic module/signal processing unit 21, a line 23 leads to an active electrode arrangement 22 which, shown here, is multi-channel and is inserted into the basal tutu of inner ear (cochlea) 7.

Portable charging device C and likewise portable wireless remote control unit 30 are added to the implant to form the entire system. For inductive recharging of implant-side battery arrangement 25, a transmitting coil 29, which is connected via a line 28 to a charging device C (as is disclosed in U.S. Pat. No. 5,274,292, which is hereby incorporated by reference to the extent necessary to complete understanding of this aspect of the invention), is temporarily placed behind the outer ear 1 near the implanted receiving means R, as is shown by an arrow in FIG. 4. Using remote control unit 30, the operating parameters of the system can be changed by the patient and can be adapted to daily ambient acoustic conditions. Basic audiologic matching takes place, likewise, transcutaneously by a programming system which communicates with the implanted telemetry means of unit E and in this manner is also able to receive information about the energy state of the battery unit.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. Implantable microphone for an implantable hearing aid which is used for excitation of hearing, comprising a microphone housing, a microphone capsule which is hermetically sealed on all sides within the microphone housing, and an electrical lead-in wire connector for routing at least one electrical connection from within the housing to outside thereof; wherein the housing has at least two legs which are arranged at an angle relative to one another, a first of said legs containing the microphone capsule and being provided with a sound inlet membrane, and a second of said legs containing the electrical lead-in wire connector and being set back relative to a plane of the sound inlet membrane.

2. Implantable microphone according to claim 1, wherein the angle between said first and second legs of the microphone housing is approximately a right angle.

3. Implantable microphone according to claim 2, wherein the microphone housing has a geometry which, when the microphone is implanted in a mastoid cavity, enables the second leg of the microphone housing to project out of the mastoid into an artificial hole in a posterior wall of the auditory canal, with the sound inlet membrane touching skin of the auditory canal wall and with the first leg of the microphone housing located in a tip area of the mastoid.

4. Implantable microphone according to claim 3, wherein an electrical connecting line is connected to the lead-in wire connector at a right angle to the first leg of the microphone housing in the area of the connection.

5. Implantable microphone according to claim 3, wherein the electrical lead-in wire connector comprises a multi-pin connector.

6. Implantable microphone according to claim 3, wherein the electrical lead-in wire connector comprises a two-pin phantom feed connector.

7. Implantable microphone according to claim 3, wherein the electrical lead-in wire connector has single-pin for carrying a useful signal potential and a power-supply DC voltage potential together; wherein the microphone housing is electrically conductive; and wherein a second pin is connected to an electrical feed line and the ground potential carried via the microphone housing.

8. Implantable microphone according to claim 1, wherein the microphone housing contains electronic components which enable electrical connection of the internal microphone capsule according to a phantom feed electrical principle.

9. Implantable microphone according to claim 1, wherein the microphone housing contains electronic components which minimize ambient electrical, and at least one of magnetic and electromagnetic influences.

10. Implantable microphone according to claim 1, wherein the microphone housing contains electronic components for at least one of electrical amplification and impedance conversion of microphone signals.

11. Implantable microphone according to claim 1, wherein the microphone housing, including the sound inlet membrane, comprises a material selected from the group consisting of pure titanium or biocompatible titanium alloys.

12. Implantable microphone according to claim 1, wherein the microphone capsule is of a type which operates according to one of the electrodynamic, electromagnetic, dielectric and electret principles.

13. Implantable microphone according to claim 1, wherein the microphone housing contains an internal semiconductor microphone.

14. Implantable microphone according to claim 4, wherein the external electrical connecting line comprises a twisted pair or coaxial line.

15. Implantable microphone according to claim 1, wherein the microphone housing has a geometry which, when the microphone is implanted in a mastoid cavity, enables the second leg of the microphone housing to project out of the mastoid into an artificial hole in a posterior wall of the auditory canal, with the sound inlet membrane touching skin of the auditory canal wall and with the first leg of the microphone housing located in a tip area of the mastoid.

16. Implantable microphone according to claim 2, wherein an electrical connecting line is connected to the lead-in wire connector at a right angle to the first leg of the microphone housing in the area of the connection.

17. Implantable microphone according to claim 16, wherein the electrical lead-in wire connector comprises a multi-pin connector.

18. Implantable microphone according to claim 16, wherein the electrical lead-in wire connector comprises a two-pin phantom feed connector.

19. Implantable microphone according to claim 16, wherein the electrical lead-in wire connector has single-pin for carrying a useful signal potential and a power-supply DC voltage potential together; wherein the microphone housing is electrically conductive; and wherein a second pin is connected to an electrical feed line and the ground potential carried via the microphone housing.

20. Implantable hearing aid for electrical stimulation of an auditory path of a person for enabling rehabilitation of at least partial impairment of at least one hearing organ, said hearing aid having an electronic signal processing and power supply systems, an implantable microphone for picking up auditory signals and stimulation means for stimulation of hearing in response to signals from said microphone, wherein said implantable microphone comprises a microphone housing, a microphone capsule which is hermetically sealed on all sides within the microphone housing, and an electrical lead-in wire connector for routing at least one electrical connection from within the housing to outside thereof; wherein the housing has at least two legs which are arranged at an angle relative to one another, a first of said legs containing the microphone capsule and being provided with a sound inlet membrane, and a second of said legs containing the electrical lead-in wire connector and being set back relative to a plane of the sound inlet membrane.

21. Implantable hearing aid according to claim 20, wherein the angle between said first and second legs of the microphone housing is approximately a right angle.

22. Implantable microphone according to claim 20, wherein the microphone housing has a geometry which, when the microphone is implanted in a mastoid cavity, enables the second leg of the microphone housing to project out of the mastoid into an artificial hole in a posterior wall of the auditory canal, with the sound inlet membrane touching skin of the auditory canal wall and with the first leg of the microphone housing located in a tip area of the mastoid.

23. Completely implantable hearing aid for electrical excitation of hearing comprising a transcutaneously rechargeable implantable battery unit, an external charging device for supplying electrical power transcutaneously to the battery unit, a remotely controllable implantable electronic unit for audiological signal processing and for monitoring and controlling the implantable battery unit, an external wireless remote control unit for controlling the implantable electronic unit, an active electrode arrangement for electrical stimulation of hearing, an implantable microphone having a microphone capsule which is accommodated in a hermetically sealed microphone housing, and an electrical lead-in wire connector for routing at least one electrical connection from the interior of the microphone housing to the implantable electronic unit;

wherein the microphone housing has at least two legs which are aligned at an angle relative to one another, one leg holding the microphone capsule and being provided with a sound inlet membrane, and the other of said two legs containing the electrical lead-in wire connector and being set back relative to a plane in which the sound inlet membrane is disposed.

24. Completely implantable hearing aid according to claim 23, wherein the microphone housing has a geometry which, when the microphone is implanted in a mastoid cavity, enables the second leg of the microphone housing to project out of the mastoid into an artificial hole in a posterior wall of the auditory canal, with the sound inlet membrane touching skin of the auditory canal wall and with the first leg of the microphone housing located in a tip area of the mastoid.

25. Completely implantable hearing aid according to claim 24, wherein the two legs of the microphone housing are roughly a right angle relative to one another.

26. Completely implantable hearing aid according to claim 23, wherein an electrical connecting line is connected to the lead-in wire connector at a right angle to the first leg of the microphone housing in the area of the connection.

27. Completely implantable hearing aid according to claim 23, wherein the microphone housing and sound inlet membrane comprise pure titanium or a biocompatible titanium alloy.

28. Completely implantable hearing aid according to claim 23, wherein the battery unit comprises at least one power cell from the group consisting of nickel-cadmium, nickel-metal-hydride, lithium or lithium ion power cells.

29. Completely implantable hearing aid according to claim 23, wherein the external charging device contains a communications means for receiving information about the energy state of the battery unit via a telemetry arrangement of the implantable electronic unit.

30. Completely implantable hearing aid according to claim 23, wherein the remote control unit has means for transmission of control data to implant-side electronics by one of inductive means and high frequency.

\* \* \* \* \*